US012594194B2

(12) United States Patent
    Coogan

(10) Patent No.: US 12,594,194 B2
(45) Date of Patent: Apr. 7, 2026

(54) EYELID CLOSURE PATCHES

(71) Applicant: FANNIN (UK) LIMITED, Swadlincote (GB)

(72) Inventor: Joseph Coogan, Belfast Antrim (GB)

(73) Assignee: FANNIN (UK) LIMITED, Swadlincote (GB)

( * ) Notice: Subject to any disclaimer, the term of this patent is extended or adjusted under 35 U.S.C. 154(b) by 815 days.

(21) Appl. No.: 17/628,173

(22) PCT Filed: Jul. 15, 2020

(86) PCT No.: PCT/GB2020/051700
    § 371 (c)(1),
    (2) Date: Jan. 18, 2022

(87) PCT Pub. No.: WO2021/014126
    PCT Pub. Date: Jan. 28, 2021

(65) Prior Publication Data
    US 2022/0257426 A1      Aug. 18, 2022

(30) Foreign Application Priority Data
    Jul. 19, 2019    (GB) ..................................... 1910338

(51) Int. Cl.
    *A61F 13/12*        (2006.01)
    *A61F 13/00*        (2024.01)
(52) U.S. Cl.
    CPC .. *A61F 13/124* (2013.01); *A61F 2013/00502* (2013.01)

(58) Field of Classification Search
    CPC .. A61F 2013/00502; A61F 2013/00497; A61F 2013/00246; A61F 2013/00251; A61F 2013/00255; A61F 13/12; A61F 13/124; A61F 13/0253; A61F 9/04
    USPC ........ 602/47, 54, 59, 74; 128/857, 858, 887, 128/888
    See application file for complete search history.

(56) References Cited

U.S. PATENT DOCUMENTS

| | | | |
|---|---|---|---|
| 5,887,590 A | 3/1999 | Price | |
| 2017/0112676 A1* | 4/2017 | Knepshield Williams | .................. A61F 13/00085 |

FOREIGN PATENT DOCUMENTS

| | | | |
|---|---|---|---|
| AU | 2014308568 B2 | 8/2018 | |
| CN | 106726128 A | 6/2013 | |
| CN | 202960933 U | 5/2017 | |
| EP | 0251737 A2 | 1/1988 | |
| EP | 0375211 A2 | 6/1990 | |
| WO | WO-2007113597 A2 * | 10/2007 | ......... A61F 13/0213 |
| WO | 2017/070270 A1 | 4/2017 | |

* cited by examiner

*Primary Examiner* — Caitlin A Carreiro
(74) *Attorney, Agent, or Firm* — Dickinson Wright PLLC

(57) ABSTRACT

An eyelid closure patch having a main body with a front face and a back face, where either one, or both, of the front face and/or the back face has a silicone adhesive at least partially covering the surface thereof. The main body can also have a semi-permeable or occlusive membrane.

13 Claims, 3 Drawing Sheets

108a/b

110a

116a/b

118

116

112

120

EYELID CLOSURE PATCHES

CROSS-REFERENCE TO RELATED APPLICATIONS

This is a US national stage application of PCT International Application No. PCT/GB2020/051700 filed on Jul. 15, 2020, which claims priority from GB 1910338.1, filed Jul. 19, 2019, the contents of which (including all attachments filed therewith) are hereby incorporated by reference in their entirety.

TECHNICAL FIELD OF THE INVENTION

The present invention relates to eyelid closure patches and methods of using the same. In particular, the invention relates to eyelid closure patches with a semi-permeable membrane and/or eyelid patches which comprise and/or are applicable with silicone adhesive, and methods of using the same.

BACKGROUND TO THE INVENTION

On average around 1 in 20 people receive surgery under general anaesthesia each year. The common practice is to tape the patient's eyelids closed using surgical adhesive tape. This tape is removed post-surgery by a nurse. This removal is known to cause skin abrasion, increasing the risk of post-surgery infection, the most common damage which can occur to the eye during and after anaesthesia.

It is not always certain why or how corneal abrasions happen during general anaesthesia. Around 6 in 10 patients do not close their eyes completely during the anaesthetic. As a result, the cornea is exposed to the air and can become dry. Also, the lacrimal gland produces fewer tears, leading to the drying of the eye. When the cornea is dry, it can stick to the inside of the eyelid, possibly leading to an abrasion when the eye is opened again.

Corneal abrasions can also occur if something rubs against the eye during the procedure. As a result, anaesthetists must take great care to ensure the eyes remain closed and protected during general anaesthesia.

The use of tape has been known to be associated with possible complications;

1. The high adhesive of the tape may stick to eyelashes and skin, causing trauma on removal.
2. The roll of tape used to secure the eyes may be reused, and a study in 1999 found over 70% of partially used tape had some bacterial growth, backed up by further research in 2012, that found over 50% of partially used tapes were contaminated with MRSA and/or VRE.

As a result of this, using traditional rolls of tape is not an ideal solution to this challenge.

U.S. Pat. No. 5,887,590 looked to solve these issues in 1997 by incorporating single-use eye pads, with a non-adhesive tab to make it easier for clinicians to use them while wearing gloves. However, there were still some issues with the adhesive being too aggressive for use around the eyes.

Further enhancements to this design in the Australian Pat. No. AU2014308568B2 aimed to solve this issue by creating an area with no/lower adhesive around the eyelash area, however this may still be tricky to apply in the right area and requires some skill to position the tab to ensure the adhesive is placed to keep the eye closed, but to not place adhesive on the closed eyelash area.

Another common use for eye pads/eyelid closure patches is in patients who suffer from dry eyes while sleeping, however existing products may 'over-adhere' due to the increased length of wear time. Also, due to the occlusive nature of films and adhesives used in the past, this could result in excessive moisture building up under the eye protectors, leading to the risk of maceration and tissue damage.

It would therefore be advantageous to provide an improved eyelid closure patch which is suitable for use at least during surgery under general anaesthesia and/or overnight (while asleep).

It would be further advantageous to provide an eyelid closure patch as above which comprises a less aggressive or more patient-friendly adhesive (e.g. causes less trauma upon removal from a subject) and/or allows for improved regulation of moisture levels within the orbital area of a subject while it is in use.

It is therefore an aim of embodiments of the invention to overcome or mitigate at least one problem of the prior art, whether described herein or not.

SUMMARY OF THE INVENTION

According to a first aspect of the invention there is provided an eyelid closure patch comprising a main body comprising a front face and a back face, wherein one of the front face and back face comprises silicone adhesive at least partially covering the surface thereof, and wherein the main body comprises a semi-permeable or occlusive membrane The closure patch or main body may comprise a suitable shape and/or size to cover and/or fit and/or conform to the orbital area of a subject.

The closure patch main body is preferably conformable (e.g. flexible or deformable), and/or hypoallergenic, and/or transparent, and preferably has adequate thickness of between 50-1000 microns to allow conformity to the periorbital area, while also maintaining sufficient thickness to maintain shape during application. The main body may comprise a coated ethyl methacrylate (EMA) or other acrylate film, over a polyurethane laminate film with an adhesive silicone backing.

The silicone adhesive may comprise a medical grade silicone adhesive, such as a medical grade soft silicone adhesive.

The medical grade silicone is a secure, yet gentle adhesive, and thus allows the product to be placed in a way that keeps a subject's eyes closed during surgery or sleep, but also allows atraumatic removal after surgery or sleep.

The silicone adhesive may be applied to the surface of the main body and/or may be at least partially impregnated or embedded into the main body on one surface thereof, which may provide a stronger interface between the main body and adhesive.

The closure patch is preferably transparent, which allows monitoring of the eye areas, in use.

The closure patch and/or silicone adhesive may be single-use or disposable to reduce the risk of cross-infection/contamination. However, this is not prejudicial to the closure patch/adhesive being able to maintain tack and adhesion after several applications, such that the patch can be removed and reapplied in order to reposition it and/or to assess the eye, such as during surgery or during the night.

In preferred embodiments, the silicone adhesive is able to adhere to dry areas (such as skin), while not adhering to moist or wet areas (such as skin or the surface of the eye). This is advantageous as the silicone adhesive will adhere to the dry areas of the eyelids and skin around the eye socket; however, it will not adhere to the moist area around the eyelashes of the closed eye. This may be an inherent property of the adhesive, but may be instead or additionally be implemented by having adhesive in particular areas or in a particular configuration on the subject and/or closure patch.

The silicone adhesive may be unperforated and/or impermeable. This may provide an occlusive layer which provides maximum moisture retention and adhesive surface area (there is a higher surface area of adhesive when unperforated), which may be useful for short term use, for example, such as short to medium length operations.

In other embodiments the silicone adhesive may be perforated (the term "perforated/perforation" is intended to cover any form of hole, pore, perforation or channel which travels through the adhesive from one side/face to the other) and/or semi-permeable. The level and/or type of perforation can be tuned to provide different permeability properties, which may be desired or required for a particular application. For example, a higher level or density of perforation, all else being equal (including the size of the perforations), will give a higher permeability per unit area to particles that can fit through those perforations, whereas larger perforations, all else being equal (including level or density of perforation) will provide increased permeability for larger particles, while having less of an effect (but not necessarily no effect) on the permeability towards smaller particles.

In order to allow an effective moisture vapour transfer rate using a waterproof but vapour permeable material, the material pores may be between 10-50 μm (micrometers), which dimensions enable prevention of the passage of water molecules at approximately 100 μm, yet allowing passage of smaller vapor molecules, for example that range from 0.0004 to 40 μm (with the smaller pores allowing less vapor to pass through than the larger pores).

Larger perforations may be useful for use over longer periods of time, such as longer operations or while sleeping overnight, as they may allow larger tear drops/tear fluid to escape such that they do not build up to undesirably high levels and/or are not trapped under the closure patch for too long.

The level and/or type of perforation can also be tuned to provide different surface area of adhesive which is in contact with the subject (such as the skin).

The closure patch may comprise different level and/or type of perforation in areas which are configured to contact the subject, than in areas which are not configured to contact the subject, for example to tailor levels of adhesion and/or permeability in these different areas.

The adhesive may cover substantially the whole front or back face of the closure patch, or may cover only a portion thereof, such as a strip, ring or border of adhesive around the perimeter of the front or back face.

The closure patch may comprise a handling tab, which may be integral with the closure patch, or may be removable from the closure patch. The handling tab preferably comprises no adhesive, but may comprise adhesive in some embodiments.

According to a second aspect of the invention there is provided an eyelid closure patch comprising a main body comprising a front face and a back face, wherein the main body comprises a semi-permeable membrane.

The semi-permeable membrane may comprise the whole main body or one or more portions thereof.

The semi-permeable membrane may extend between the front face and back face of the closure patch.

The semi-permeable membrane may be continuous or may comprise a number of semi-permeable areas which are spaced apart from, and unconnected to, one another, such as a pattern, array or matrix of semi-permeable areas.

The semi-permeable membrane may cover or span at least 40%, 50%, 60%, 70%, 80% or 90%, or substantially 100%, of the surface area or cross-sectional area of the closure patch, main body and/or front and/or back face.

The semi-permeable membrane may comprise a semi-permeable film membrane.

The semi-permeable membrane is preferably conformable (e.g. flexible or deformable), and/or hypoallergenic, and/or transparent, and preferably has a thickness of between 50-1000 microns to allow conformity to the peri-orbital area, while also maintaining sufficient thickness to maintain shape during application. The semi-permeable membrane may comprise a coated ethyl methacrylate (EMA) or other acrylate film, over a polyurethane laminate film, and comprising pores therethrough.

The semi-permeable membrane may comprise a porous network and/or a number of pores, holes, channels or perforations extending therethrough from one side or face to the other, such as from one face of the main body to the other, or from one side of an adhesive to the other. In embodiments wherein the closure patch comprises a semi-permeable adhesive on one face thereof, and also comprises a semi-permeable membrane as part of the main body (including the main body being a semi-permeable membrane), at least some of the pores, holes, channels or perforations of one component may be in fluid communication with at least some of those of the other component, such that there is a continuous membrane formed in areas where respective portions of the adhesive and semi-permeable membrane/main body abut each other or are adjacent to each other.

The advantages, features and principles of the permeability of the or each semi-permeable membrane may be substantially as described in relation to those described in relation to the perforated adhesive above, the comments being applied mutatis mutandis to the or each semi-permeable membrane.

Provision of a closure patch with both a semi-permeable membrane which comprises a portion of or the whole of the main body (and which may extend between the front face and the back face), and a second semi-permeable membrane in the form of a perforated silicone adhesive, allows for even finer tuning of permeability/breathability vs. adhesive properties/strength.

According to a third aspect of the invention there is provided a method of applying an eyelid closure patch to a subject, the method comprising;
  a) providing an eyelid closure patch of the first aspect of the invention; and
  b) securing the eyelid closure patch to the orbital area of a subject using medical grade silicone adhesive.

The method may comprise providing a closure patch in step a) which comprises medical grade silicone adhesive as part thereof (on the front or back face), or the method may instead comprise applying said adhesive to a face of a closure patch and/or to the orbital area of a subject, and subsequently applying the closure patch to the subject.

The method may comprise a further step c) of removing the closure patch from the subject. The closure patch comprises a silicone adhesive (which sticks the closure patch to the subject), such as a soft silicone adhesive, and step c) may comprise removing the closure patch without causing trauma, significant trauma or substantial trauma to the subject and/or the orbital area of the subject.

According to a fourth aspect of the invention there is provided an eyelid closure patch kit comprising at least one eyelid closure patch and a closure patch retaining member.

The or each closure patch may comprise a closure patch of the first aspect of the invention.

The kit may comprise at least two closure patches, such as at least one pair of closure patches.

The retaining member may comprise a release layer or liner. The or each closure patch may be releasably secured to the release layer. In some embodiments, the or each closure patch is releasably secured to a release layer by means of an adhesive, such as a silicone adhesive, preferably a silicone adhesive, which is preferably a soft and/or medical grade silicone adhesive.

In some embodiments, the or each closure patch comprise a handling tab, which is preferably not secured to the release layer. The handling tab allows easier removal of a closure patch from the release layer.

In some embodiments, the kit may comprise a sterile/sterilisation/sterilised pouch. The pouch may comprise a release layer as described above, and may comprise a release layer with the or each closure patch releasably secured thereto, as described above. The pouch may comprise a base on which the release layer is located (or alternatively the release layer may comprise the base or be formed as part of the base). The pouch may comprise a sealing member, such as a sealing film, configured, in use, to form a sealed inner cavity of the pouch, in which the or each closure patch is located.

The sealing member may be sealed to the base and/or release layer. In other embodiments, the sealing member may additionally or alternatively be sealed to itself to form a substantial bag, pouch or wrapping around the base, closure patch(es) and/or release layer.

The semi-permeable membrane and silicone adhesive of the eyelid closure patch of the invention may in some embodiments be one-and-the-same, but in other embodiments they may be distinct components of the closure patch. In embodiments wherein the silicone adhesive is perforated and/or semi-permeable, they may combine to form a substantially continuous semi-permeable membrane in areas where respective portions of the adhesive and semi-permeable membrane/main body abut each other or are adjacent to each other.

DETAILED DESCRIPTION OF THE INVENTION

In order that the invention may be more clearly understood one or more embodiments thereof will now be described, by way of example only, with reference to the accompanying drawings, of which:

Figure 1:
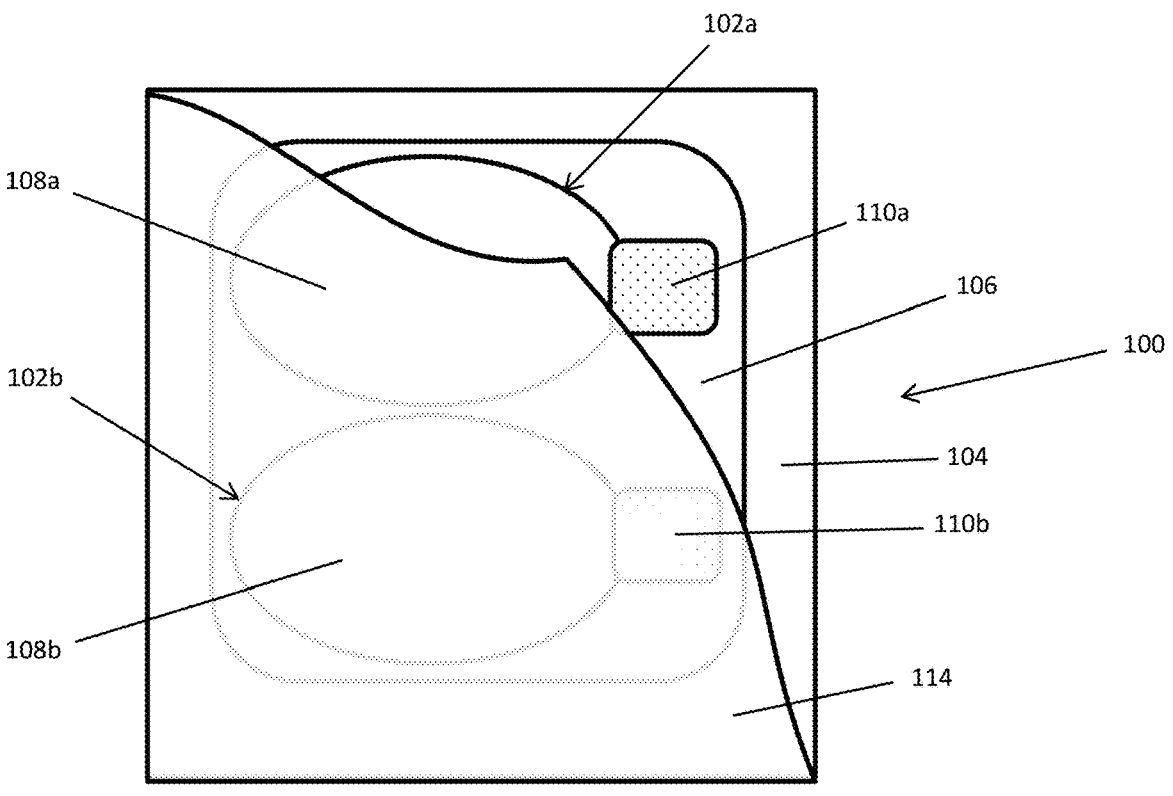
FIG. 1 illustrates a top-down view of a protective sterilisation pouch of an embodiment of the third aspect of the invention, which contains a pair of eyelid closure patches, each of an embodiment of the first aspect of the invention
Figure 2:
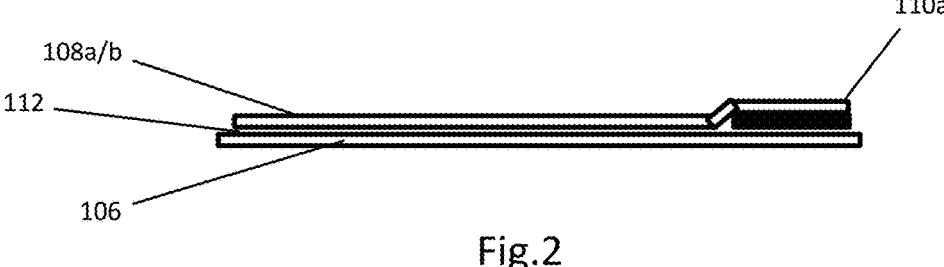
FIG. 2 is a side view of the eyelid closure patches and release liner of FIG. 1
Figure 3:
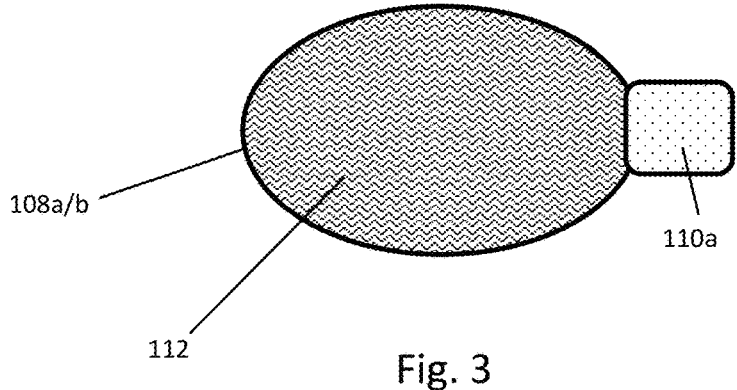
FIG. 3 is a bottom-up view of one of the eyelid closure patches of FIG. 1
Figure 6:
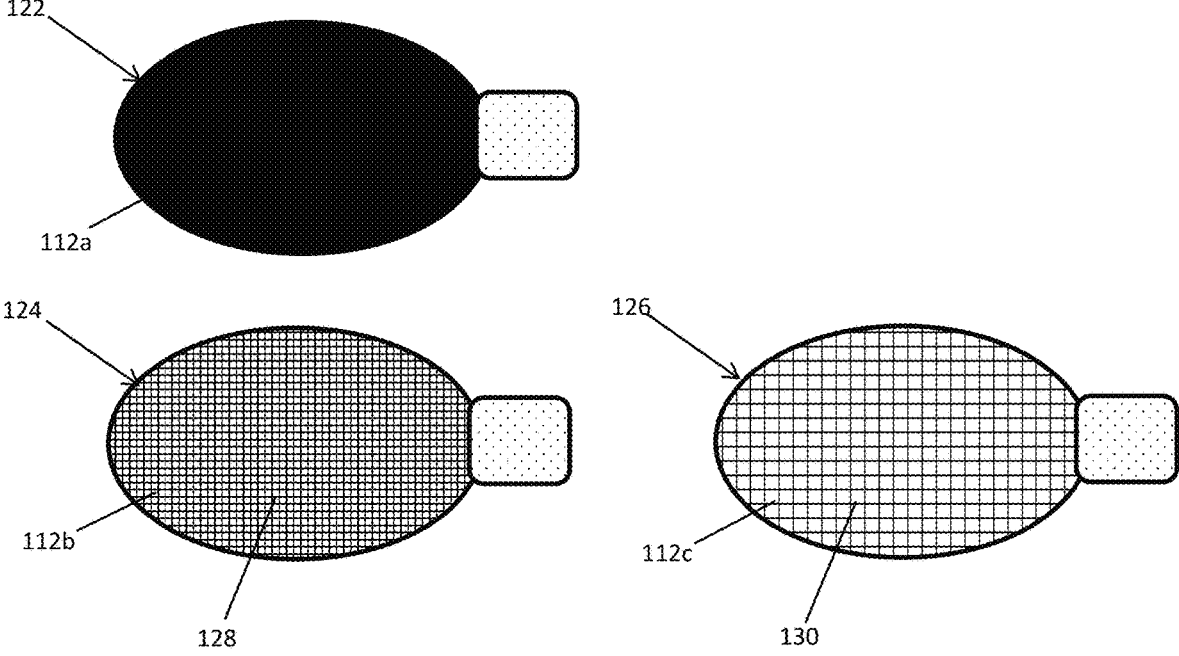

FIG. 6 illustrates three further embodiments of eyelid closure patches of the first aspect of the invention, each comprising adhesive with a different level of perforation FIG. 1 illustrates a top-down view of a protective sterilisation pouch 100 of an embodiment of a kit of the third aspect of the invention, which contains a pair of eyelid closure patches 102a, 102b, each of an embodiment of the first aspect of the invention. The pouch 100 comprises a base 104 on which a release liner, consisting of a siliconized LDPE-paper liner 106 is located. The two eyelid closure patches 102a, 102b are releasably attached to the release liner 106. The closure patches 102a, 102b each comprise a main body 108a, 108b (coated EMA Film, over a polyurethane duo laminate film, with an adhesive silicone backing) which has an integrated non-adhesive tab 110a, 110b. As can be seen in FIG. 2, the main body 108a, 108b of the closure patches 102a, 102b and non-adhesive tabs 110a lie on top of the release liner 106. The closure patches 102a, 102b are releasably secured to the release liner 106 by medical grade soft-silicone adhesive 112 which covers the entire back surface of each closure patch 102a, 102b (as is also illustrated in FIG. 3). The pouch 100 further comprises a sealing film 114 which, in use, is sealed to the base 104 around the entire periphery thereof, in order to fully seal the interior of the pouch 100 which contains the closure patches 102a, 102b, which are releasably secured to the release liner 106.

Figure 4:
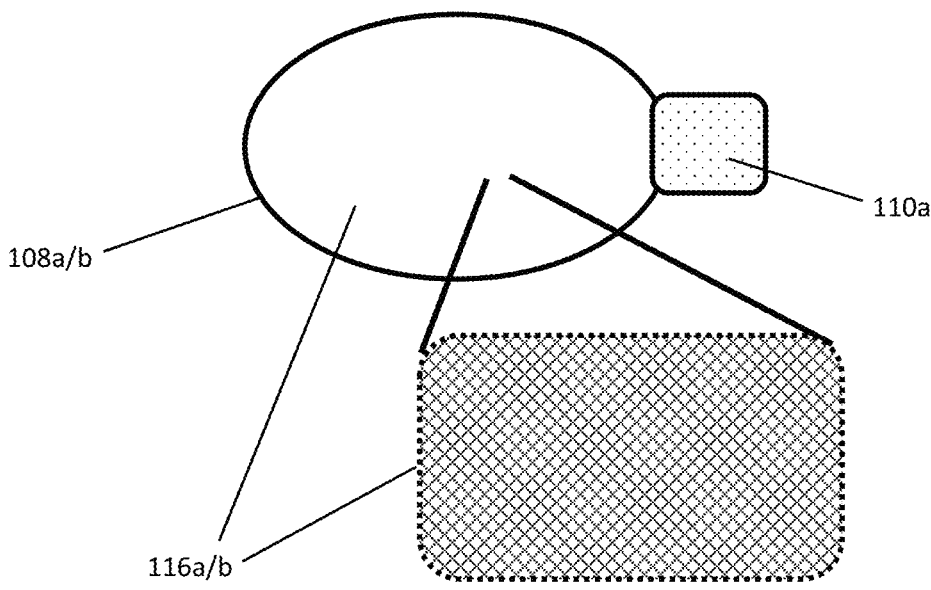
FIG. 4 is a top down view of one of the eyelid closure patches of FIG. 1, comprising a zoomed-in view illustrating the semi-permeable membrane thereof
Figure 5:
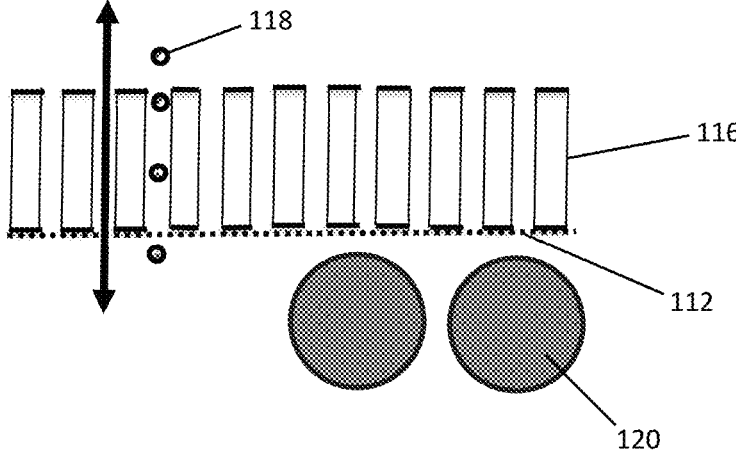
FIG. 5 illustrates the function of the semi-permeable membrane of the eyelid closure patches of FIG. 1

The main body 108a, 108b of each closure patch 102a, 102b, as is illustrated in FIG. 4, comprises a semi-permeable film membrane 116a, 116b comprising EMA over a polyurethane duo laminate film. As can be seen in FIG. 5, the semi-permeable membrane 116 allows smaller liquid or vapour particles 118, such as excessive moisture vapours, to pass through, but blocks passage of larger liquid particles or droplets 120, such as tear drops. The closure patches 102a, 102b are thus able to allow excess moisture or moisture vapours in the orbital area of a subject to escape, while trapping tear fluid in said area.

Also shown in FIG. 5 is the perforated nature of the silicone adhesive 112. Varying level and/or type of perforation in the adhesive 112 allows for even finer control over relative permeability of the closure patches 102a, 102b to e.g. liquid, moisture and/or vapours, and also allows a level of control over the surface area of adhesive 112 that is in contact with the skin of a subject when in use.

FIG. 6 illustrates bottom-up views of the reverse side/rear face of three further embodiments of closure patches of the first and second aspects of the invention 122, 124, 126, each comprising a different level and/or type of perforation in the silicone adhesive 112a, 112b, 112c thereof. Closure patch 122 comprises non-perforated silicone adhesive 112a which has low or no vapour permeability and covers substantially the whole surface area of the back face of the closure patch 122. Closure patch 124 comprises perforated silicone adhesive 112b which comprises medium-sized perforations 128 and which covers a lower surface area of the back surface of the closure patch 124 (compared to closure patch 122). The medium-sized perforations 128 give the adhesive 112b a medium level of permeability. Closure patch 126 comprises perforated silicone adhesive 112c which comprises large perforations 130 and which covers an even lower surface area of the back surface of the closure patch 126 (in comparison to closure patches 122 and 124). The large perforations 130 give the adhesive 112c a high level of permeability (e.g. larger particles can pass through which could not pass through the medium-sized perforations 128 of closure patch 124). Thus, the different types/levels of perforation of the silicone adhesive allows the permeability properties thereof to be tuned, for example depending on the desired use and/or the desired closure patch properties.

The one or more embodiments are described above by way of example only. Many variations are possible without departing from the scope of protection afforded by the appended claims.

The invention claimed is:

1. An eyelid closure patch comprising a main body comprising a front face and a back face, wherein one of the front face and back face comprises silicone adhesive at least partially covering or comprising one surface thereof, and wherein the main body comprises a semi-permeable membrane, wherein the semi-permeable membrane comprises a plurality of pores, holes, channels or perforations extending therethrough from one side or face of the membrane to another side or face of the membrane, wherein the plurality of pores, holes, channels or perforations have a diameter of at least 10 μm and smaller than 50 μm.

2. The eyelid closure patch as claimed in claim 1, wherein the semi-permeable membrane and silicone adhesive are distinct components of the eyelid closure patch, and the silicone adhesive is perforated and/or semi-permeable.

3. The eyelid closure patch as claimed in claim 2, wherein the semi-permeable membrane and perforated and/or semi-permeable silicone adhesive together form a substantially continuous semi-permeable membrane in areas where respective portions of the adhesive and semi-permeable membrane/main body abut each other or are adjacent to each other.

4. The eyelid closure patch as claimed in claim 1, wherein the semi-permeable membrane comprises the silicone adhesive.

5. The eyelid closure patch as claimed in claim 1, wherein the semi-permeable membrane comprises the whole main body or one or more portions thereof.

6. The eyelid closure patch as claimed in claim 1, wherein the semi-permeable membrane extends between the front face and back face of the main body.

7. The eyelid closure patch as claimed in claim 1, wherein the semi-permeable membrane covers or spans at least 60% of the surface area or cross-sectional area of the eyelid closure patch, main body and/or front and/or back face.

8. The eyelid closure patch as claimed in claim 1, wherein the plurality of pores, holes, channels or perforations extend from one face of the main body to the other.

9. The eyelid closure patch as claimed in claim 1, wherein the main body is conformable, flexible, deformable, hypo-allergenic, and/or transparent.

10. The eyelid closure patch as claimed in claim 1, wherein the silicone adhesive comprises medical grade silicone adhesive.

11. The eyelid closure patch as claimed in claim 1, wherein the silicone adhesive is applied to a surface of the main body and/or comprises a layer on the surface of the main body and/or is at least partially impregnated or embedded into the surface of the main body.

12. The eyelid closure patch as claimed in claim 1, wherein the channels or perforations have the diameter from 0.0004 to 40 μm.

13. A method of applying an eyelid closure patch to a subject, the method comprising;

a) providing an eyelid closure patch of claim 1; and b) securing the eyelid closure patch to the orbital area of a subject using the silicone adhesive of the eyelid closure patch.

* * * * *